(12) United States Patent
Waki

(10) Patent No.: US 8,469,892 B2
(45) Date of Patent: Jun. 25, 2013

(54) ULTRASONIC DIAGNOSTIC APPARATUS AND METHOD OF DISPLAYING ULTRASONIC IMAGE

(75) Inventor: Koji Waki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/062,769

(22) PCT Filed: Jun. 22, 2009

(86) PCT No.: PCT/JP2009/061290
§ 371 (c)(1),
(2), (4) Date: Mar. 8, 2011

(87) PCT Pub. No.: WO2010/026823
PCT Pub. Date: Mar. 11, 2010

(65) Prior Publication Data
US 2011/0178404 A1 Jul. 21, 2011

(30) Foreign Application Priority Data
Sep. 8, 2008 (JP) ................................ 2008-229179

(51) Int. Cl.
*A61B 8/00* (2006.01)

(52) U.S. Cl.
USPC ............................ 600/438; 600/437; 600/443

(58) Field of Classification Search
USPC ................................................. 600/437–469
See application file for complete search history.

(56) References Cited

U.S. PATENT DOCUMENTS

| 8,094,911 | B2 * | 1/2012 | Lindop et al. ................. 382/131 |
| 8,098,921 | B2 * | 1/2012 | Matsumura ................... 382/133 |
| 2006/0184020 | A1 * | 8/2006 | Sumi .............................. 600/437 |
| 2007/0244390 | A1 * | 10/2007 | Matsumura .................... 600/437 |
| 2009/0292205 | A1 * | 11/2009 | Osaka ............................. 600/443 |
| 2010/0016724 | A1 * | 1/2010 | Arai et al. ...................... 600/443 |
| 2010/0036243 | A1 * | 2/2010 | Matsumura .................... 600/438 |
| 2010/0113937 | A1 * | 5/2010 | Matsumura et al. .......... 600/462 |
| 2010/0191111 | A1 * | 7/2010 | Azuma .......................... 600/438 |
| 2010/0220901 | A1 * | 9/2010 | Matsumura .................... 382/128 |
| 2010/0268084 | A1 * | 10/2010 | Osaka et al. .................. 600/443 |
| 2010/0324421 | A1 * | 12/2010 | Waki et al. .................... 600/443 |
| 2011/0204893 | A1 * | 8/2011 | Sumi ............................. 324/318 |

FOREIGN PATENT DOCUMENTS

| JP | 2000-060853 | 2/2000 |
| JP | 2006-271523 | 10/2006 |
| JP | 2007-105400 | 4/2007 |
| JP | 2007-125152 | 5/2007 |

(Continued)

*Primary Examiner* — Sanjay Cattungal
(74) *Attorney, Agent, or Firm* — Antonelli, Terry, Stout & Kraus, LLP.

(57) ABSTRACT

Provided are an ultrasonic diagnostic apparatus that constructs and displays a 3-dimensional elastic image showing the hardness or softness of a biological tissue in an object to be examined, and a method of displaying an ultrasonic image. The ultrasonic diagnostic apparatus is provided with an RF signal frame data storing unit (20) that stores a predetermined range of RF signal frame data based on the reflected echo signals received by the reception unit (4), an RF signal frame data selecting unit (21) that selects the RF signal frame data in the predetermined range stored in the RF signal frame data storing unit (20), an elasticity information calculating unit (23) that calculates strain or elastic modulus from the RF signal frame data in the predetermined range, and a 3-dimensional elastic image constructing unit (28) that constructs a 3-dimensional elastic image on the basis of the calculated strain or elasticity modulus.

13 Claims, 11 Drawing Sheets

FOREIGN PATENT DOCUMENTS

| | | |
|---|---|---|
| WO | WO 2006/013916 A1 | 2/2006 |
| WO | WO 2006/106852 A1 | 10/2006 |
| WO | WO 2006/121031 A1 | 11/2006 |

* cited by examiner

FIG. 2
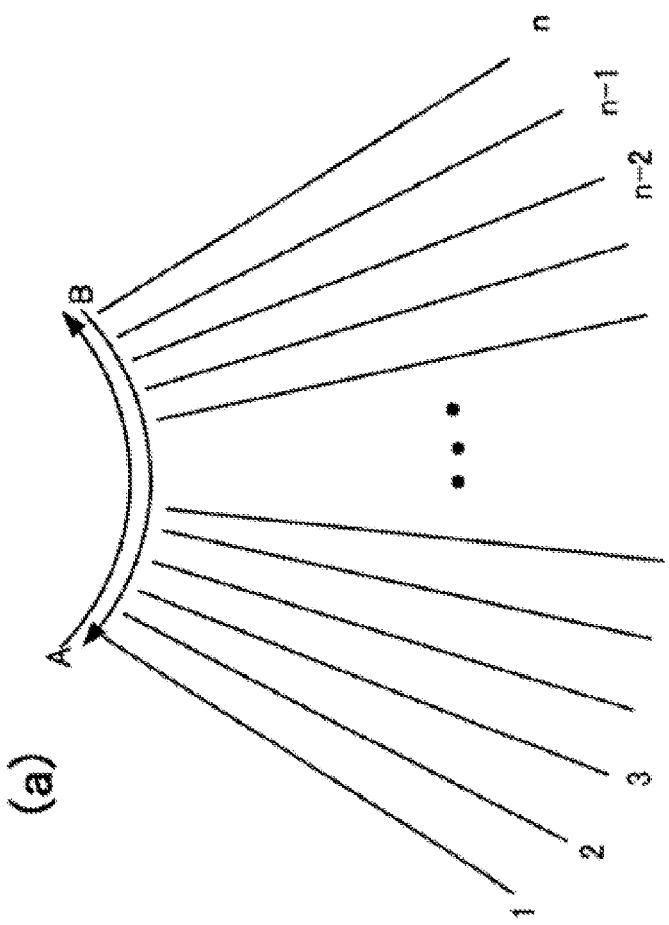
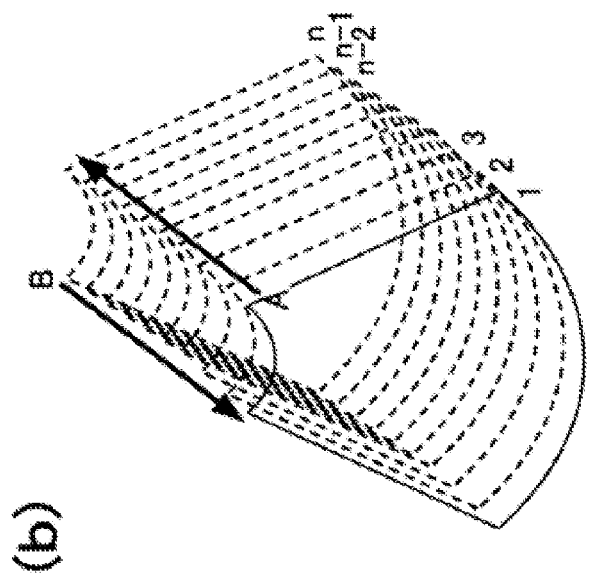

FIG. 3
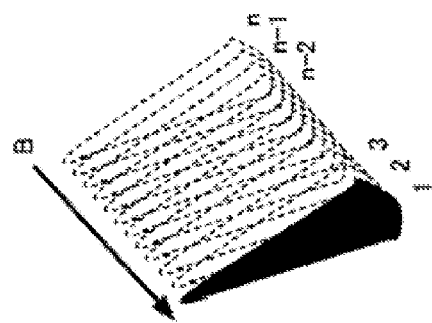
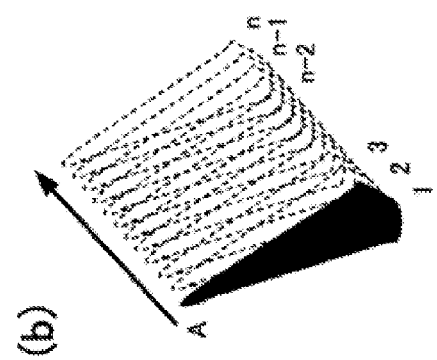
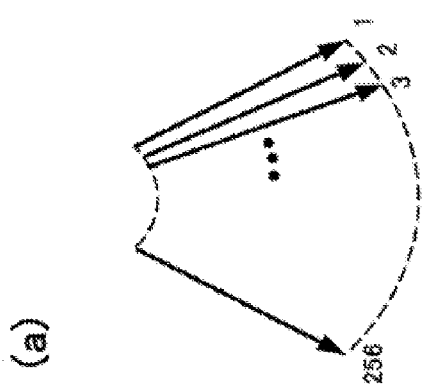
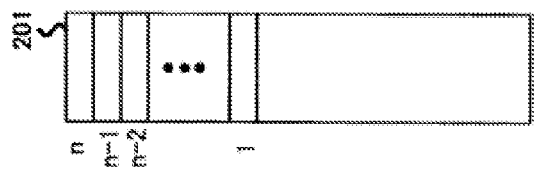
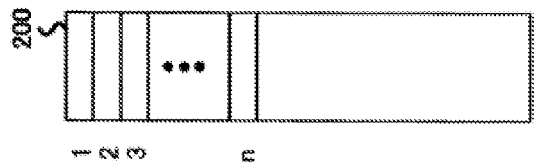

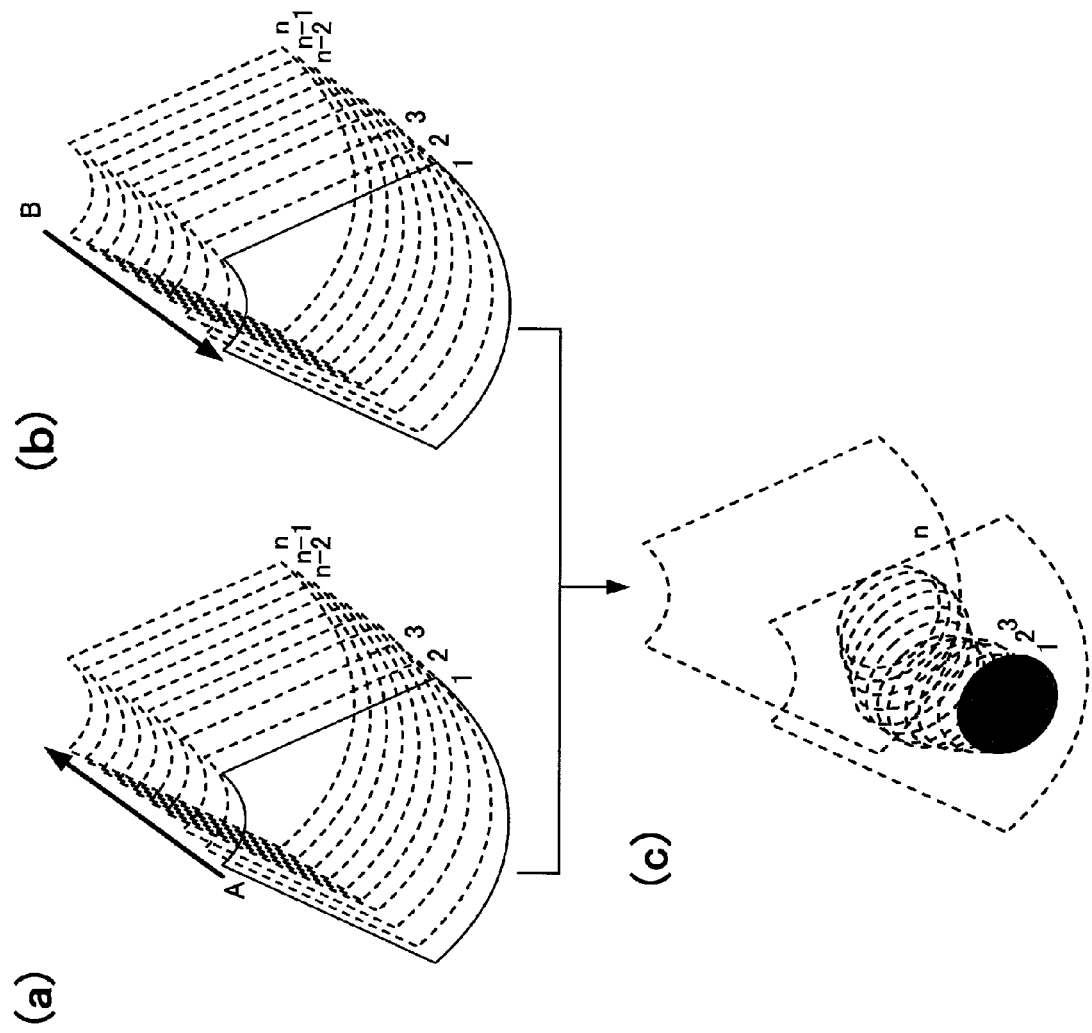

ULTRASONIC DIAGNOSTIC APPARATUS AND METHOD OF DISPLAYING ULTRASONIC IMAGE

FIELD OF THE INVENTION

The present invention relates to an ultrasonic diagnostic apparatus and ultrasonic image display method for displaying an elastic image showing hardness or softness of biological tissues in an object to be examined using ultrasonic waves.

DESCRIPTION OF RELATED ART

An ultrasonic diagnostic apparatus transmits ultrasonic waves to the inside of an object by an ultrasonic probe, constructs and displays, for example a tomographic image based on the reception signals received from biological tissues in the object. Also, it measures the reception signals received from the biological tissues in the object using the ultrasonic probe, and obtains the displacement in each area of the biological object from the RF signal frame data of two reception signals measured at different times. An elastic image showing elasticity modulus of biological tissues is then constructed based on the obtained displacement data (for example, Patent Document 1).

Also, it has a position sensor that measures position and tilt of the ultrasonic probe at the same time of transmitting and receiving ultrasonic waves, generates volume data from the positional information acquired by the position sensor and a plurality of 2-dimensional tomographic images, and displays a 3-dimensional tomographic image (for example, Patent Document 2).

Prior Art Documents

Patent Document 1: JP-A-2000-060853
Patent Document 2: JP-A-2006-271523

However, the technique disclosed in Patent Document 1 only constructs a 2-dimensional elastic image, and the technique for constructing a 3-dimensional elastic image is not disclosed in concrete terms. Therefore, construction of a 3-dimensional elastic image requires a tremendous amount of calculation and memory capacity, and is impossible to achieve merely by extending the technique for constructing a 3-dimensional tomographic image disclosed in Patent Document 2.

The objective of the present invention is to construct and display a 3-dimensional elastic image showing hardness or softness of biological tissues in an object.

BRIEF SUMMARY OF THE INVENTION

In order to achieve the above-described objective, the present invention comprises:

an ultrasonic probe having transducers that transmit and receive ultrasonic waves;

a transmission unit configured to transmit ultrasonic waves to an object to be examined via the ultrasonic probe;

a reception unit configured to receive the reflected echo signals from the object;

an RF signal frame data storing unit configured to store a predetermined range of RF signal frame data based on the reflected echo signals received by the reception unit;

an RF signal frame data selecting unit configured to select the predetermined range of RF signal frame data stored in the RF signal frame data storing unit;

an elasticity information calculating unit configured to calculate strain or elasticity modulus from the predetermined range of RF signal frame data;

a 3-dimensional elastic image constructing unit configured to construct a 3-dimensional elastic image based on the calculated strain or elasticity modulus; and a display unit configured to display the 3-dimensional elastic image.

Accordingly, a 3-dimensional elastic image showing hardness or softness of biological tissues in an object can be constructed.

EFFECT OF THE INVENTION

In accordance with the present invention, it is possible to construct a 3-dimensional image showing hardness or softness of biological tissues in an object to be examined.

BRIEF DESCRIPTION OF THE DRAWINGS

FIG. 2 shows a storage pattern of tomographic image data related to the present invention.

FIG. 3 shows the detail of an RF signal frame data storing unit in a first embodiment of the present invention.

FIG. 11 shows the pattern for generating 2-dimensional elastic image data in the fourth embodiment of the present invention.

DETAILED DESCRIPTION OF THE INVENTION (First Embodiment: Raster Address)

Figure 1:
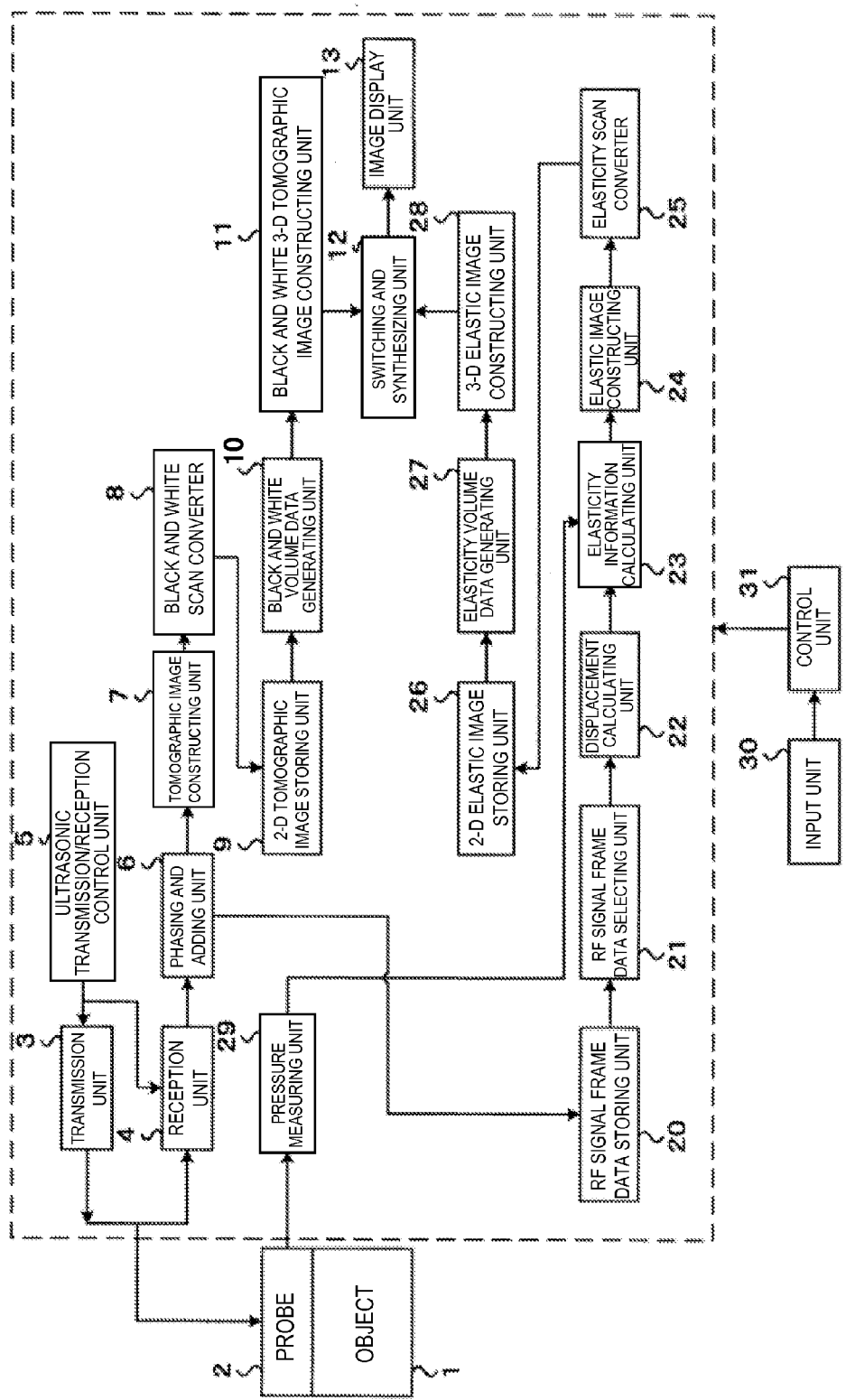
FIG. 1 is a block diagram showing a general configuration of the present invention.

The ultrasonic diagnostic apparatus to which the present invention is applied will be described referring to FIG. 1. As shown in FIG. 1, the ultrasonic diagnostic apparatus comprises:

ultrasonic probe 2 to be used by applying to object 1;

transmission unit 3 configured to repeatedly transmit ultrasonic waves to object 1 at time intervals via ultrasonic probe 2;

reception unit 4 configured to receive the reflected echo signals generated from object 1 in time series;

ultrasonic transmission/reception control unit 5 configured to control switching of transmission and reception of transmission unit 3 and reception unit 4; and phasing and adding unit 6 configured to execute phasing and adding of the reflected echo signals received by reception unit 4.

Ultrasonic probe 2 is formed by a plurality of transducers disposed therein, and has the function that transmits and receives ultrasonic waves via the transducers. Ultrasonic probe 2 is capable of mechanically vibrating the plurality of transducers in the direction orthogonal to the array direction thereof and transmitting/receiving ultrasonic waves. Also, ultrasonic probe 2 has a position sensor that measures tilt of the transducer at the same time of transmitting and receiving ultrasonic waves, and outputs the tilt of the transducer as a frame number. Ultrasonic probe 2 may also have configuration that a plurality of transducers are 2-dimensionally arrayed and the directions of transmitting/receiving ultrasonic waves can be electrically controlled.

In this manner, ultrasonic probe 2 mechanically and electrically vibrates a plurality of transducers in the direction orthogonal to the array direction thereof, and transmits/receives ultrasonic waves. Transmission unit 3 generates transmitting pulses for generating ultrasonic waves by driving the transducers of ultrasonic probe 2. Transmission unit 3 has the function to set the conversion point of the transmitted ultrasonic waves at a certain depth. Also, reception unit 4 generates RF signals, i.e. reception signals by amplifying the reflected echo signals received by ultrasonic probe 2 at a predetermined gain. Ultrasonic transmission/reception control unit 5 controls transmission unit 3 or reception unit 4.

Phasing and adding unit 6 executes phase control by inputting the RF signals amplified in reception unit 4, and generates the RF signal frame data by forming an ultrasonic beam with respect to one or a plurality of focusing points.

Tomographic image constructing unit 7 obtains tomographic image data by inputting the RF signal frame data from phasing and adding unit 6 and executing signal processing such as gain compensation, log compression, detection, edge enhancement and filtering. Also, black and white scan converter 8 executes coordinate system conversion of tomographic image data in order to display the tomographic image data synchronized with scanning of ultrasonic waves using the display system of image display unit 13.

2-dimensional tomographic image storing unit 9 stores the tomographic image data outputted from black and white scan converter 8 along with the frame numbers as shown in FIG. 2. Here, an ultrasonic wave is transmitted and received by mechanically vibrating transducers in the direction orthogonal to the array direction thereof, and the tomographic image data of n-frame is obtained with respect to the scan in A-direction and B-direction.

FIG. 2(a) shows 3-dimensional acquisition of tomographic image data while assuming 2-dimensional tomographic image data as one line in the frame direction. FIG. 2(b) shows 3-dimensional acquisition of 2-dimensional tomographic image data.

The frame numbers correspond the position (tilt) of the plurality of transducers to the tomographic image data as shown in FIG. 2(a). The first frame number of the scan in A-direction is set as "1", and the last frame number is set as "n". The tomographic image data of frame number "1" is first stored in 2-dimensional tomographic image storing unit 9, and then the tomographic image data of frame number "2" is stored in 2-dimensional tomographic image storing unit 9. Then the tomographic image data of frame number "n" is finally stored in 2-dimensional tomographic image storing unit 9. Also, the first frame number of the scan in B-direction is set as "n" and the last frame number is set as "1", and the tomographic image data is stored in 2-dimensional tomographic image storing unit 9.

Black and white volume data generating unit 10 reads out the tomographic image data for the portion of n-frame stored in 2-dimensional tomographic image storing unit 9, and generates the black and white volume data by sequentially disposing the data for each scan plane. In this manner, the black and white volume data for the rendering which is the collection of tomographic image data in the object is constructed.

Black and white 3-dimensional tomographic image constructing unit 11 reads out black and white volume data from black and white volume data generating unit 10, and constructs a black and white 3-dimensional tomographic image by projecting the black and white volume data on a plane. In concrete terms, black and white 3-dimensional tomographic image constructing unit 11 obtains image information of each point in the black and white volume data from the luminance value and the opacity corresponding to the respective points (coordinates). Then black and white 3-dimensional tomographic image constructing unit 11 constructs a black and white 3-dimensional tomographic image using the volume rendering method by the equation below that gives contrasting density by calculating the luminance value and the opacity of the black and white volume data of the view point direction in the depth direction.

$$\alpha_{outi} = \alpha_{ini} + (1-\alpha_{ini}) \times \alpha_i$$

$$C_{outi} = C_{ini} + (1-\alpha_{ini}) \times \alpha_i \times C_i \qquad \text{[Equation 1]}$$

$\alpha_{outi}$: output of the i-th opacity
$\alpha_{ini}$: input of the i-th opacity
$\alpha_i$: the i-th opacity
$C_{outi}$: output of the i-th luminance
$C_{ini}$: input of the i-th luminance
$C_i$: the i-th luminance While the volume rendering method is used above for constructing a black and white 3-dimensional tomographic image, other methods may be used such as the surface rendering method that gives contrasting density according to the tilt angle formed by the pixel in each point with respect to the plane corresponding to the view point position or the voxel method that gives contrasting density according to the depth of an object viewed from the view point position.

Also, the ultrasonic diagnostic apparatus comprises switching and synthesizing unit 12 that synthesizes a black and white 3-dimensional tomographic image and a color 3-dimensional elastic image to be described later, juxtaposes and switches the images, and image display unit 13 that displays a black and white 3-dimensional tomographic image, a color 3-dimensional elastic image and the synthesized image in which a black and white 3-dimensional tomographic image and a color 3-dimensional elastic image are synthesized.

Further, the ultrasonic diagnostic apparatus comprises RF signal frame data storing unit 20 that stores the RF signal frame data outputted from phasing and adding unit 6, RF signal frame data selecting unit 21 that selects at least two sets of RF signal frame data stored in RF signal frame data storing unit 20, displacement calculating unit 22 that measures displacement of biological tissues in object 1 from two sets of RF signal frame data, elasticity information calculating unit 23 that acquires elasticity information such as strain or elasticity modulus from the displacement information measured in displacement calculating unit 22, elastic image constructing unit 24 that constructs 2-dimensional elastic image data from the strain or elasticity modulus calculated in elasticity information calculating unit 23, and elastic scan converter 25 that executes coordinate system conversion on the 2-dimensional elastic image data outputted from elastic image constructing unit 24 for displaying the data by the display system of image display unit 13.

In the present embodiment, the ultrasonic diagnostic apparatus further comprises 2-dimensional elastic image storing unit 26 that stores the 2-dimensional elastic image data outputted from elasticity scan converter 25, elastic volume data generating unit 27 that generates elastic volume data from plural sets of 2-dimensional elastic image data, and 3-dimensional elastic image constructing unit 28 that constructs a color 3-dimensional elastic image from elastic volume data.

Also, the ultrasonic diagnostic apparatus comprises control unit 31 that controls the respective components, and input unit 30 that executes various inputs to control unit 31. Input unit 30 comprises devices such as a keyboard or trackball.

Figure 4:
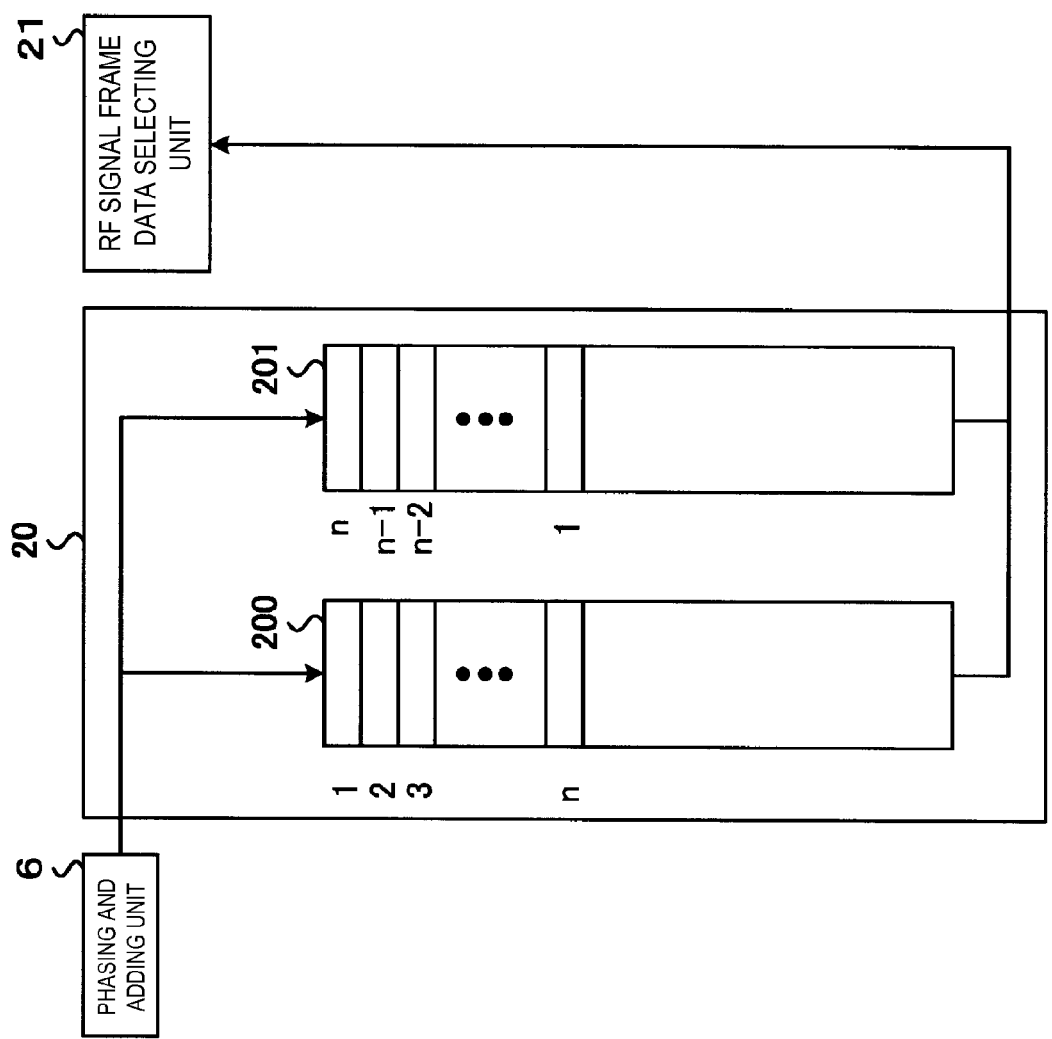
FIG. 4 shows the detail of an RF signal frame data storing unit in the first embodiment of the present invention.

RF signal frame data storing unit 20 sequentially stores the RF signal frame data generated from phasing and adding unit 6 in time series. FIG. 3 and FIG. 4 show the detail of RF signal frame data storing unit 20.

In the present embodiment, RF signal frame data storing unit 20 has storage media 200 that stores the RF signal frame data related to the scan in the A-direction and storage media 201 that stores the RF signal frame data related to the scan in the B-direction.

In concrete terms, storage media 200 and storage media 201 stores the RF signal frame data in a plurality of ultrasonic transmission/reception directions, i.e. a plurality of raster addresses. The raster address corresponds to the data on a scan line (arrow) of a piece of RF signal frame data shown in FIG. 3(a). When the entire raster address is set as "256", storage media 200 and storage media 201 stores, for example the RF signal frame data of the raster address in the set range of "1"~"50".

The set range can be arbitrarily set, wherein the RF signal frame data in the raster address of "50"~"200" can be stored in storage media 200 and storage media "200" or the RF signal frame data in the raster address of "100"~"150" can be stored in storage media 200 and storage media 201.

Then storage media 200 that stores the RF signal frame data related to the scan in A-direction stores the RF signal frame data in the raster address of the range set as mentioned above for the portion of the scan in A-direction.

FIG. 3(b) shows the relationship between the RF signal frame data of the raster address in the set range of the scan in A-direction and the frame number, and FIG. 3(d) shows the storage pattern of storage media 200 that stores the RF signal frame data in the raster address of the set range of the scan in A-direction while corresponding the data to the frame number.

Storage media 200 stores RF signal frame data by setting the first frame number of the scan in the A-direction as "1" and setting the last frame number as "n". Concretely, the RF signal frame data of the scan in the A-direction having frame number "1" is first stored in storage media 200, and then the RF signal frame data of frame number "2" is stored in storage media 200. Then the RF signal frame data having frame number "n" is finally stored in storage media 200. Then the RF signal frame data having frame number "n" is finally stored in storage media 200.

Also, storage media 201 that stores the RF signal frame data related to the scan in the B-direction stores the RF signal frame data of the raster address in the same set range as in the storage media 200, for the portion of the scan in B-direction.

FIG. 3(c) shows the relationship between the RF signal frame data of the raster address in the set range of the scan in the B-direction and the frame number, and FIG. 3(e) shows the storage pattern of storage media 201 that stores the RF signal frame data in the raster address of the set range of the scan in the B-direction while corresponding the to the frame number. Storage media 201 stores the RF signal frame data by setting the first frame number of the scan in the B-direction as "n" and setting the last frame number as "1". Concretely, the RF signal frame data of the scan in the B-direction having frame number "n" is first stored in storage media 201, and then the RF signal frame data of frame number "n−1" is stored in storage media 201. Then the RF signal frame data of frame number "1" is finally stored in storage media 201.

While RF signal frame data storing unit 20 has two storage media 200 and 201 in the above, RF signal frame data may also be sorted and stored in one storage media.

As shown in FIG. 4, RF signal frame data selecting unit 21 selects the RF signal frame data of frame number "N" stored in storage media 200 of RF signal frame data storing unit 20. N is a positive integer which is greater or equal to 1 and less or equal to "n". Then RF signal frame data selecting unit 21 selects the RF signal frame data of frame number "N" stored in storage media 201 which is the same frame number "N" of the RF signal frame data read out from storage media 200.

Then displacement calculating unit 22 executes one-dimensional or two dimensional correlation processing from the selected RF signal frame data of frame number "N", and obtains one-dimensional or two-dimensional displacement distribution related to the displacement or moving vector, i.e. the direction and size of the displacement in the biological tissues corresponding to each point of the RF signal frame data. Here, the block matching method is used for detecting the moving vector. The block matching method divides an image into blocks formed by, for example M×M pixels, focuses on a block within the region of interest, searches the block which is most approximated to the focused block from the previous frame, and executes the process to determine the sample value by predictive coding, i.e. the difference referring to the searched block.

Elasticity information calculating unit 23 calculates strain or elasticity modulus of the biological tissues corresponding to each point (coordinates) on the image from the measured value outputted from displacement calculating unit 22 such as the moving vector and the pressure value outputted from pressure measuring unit 26, and generates elasticity information. At this time, the strain is calculated by performing spatial differentiation on the distance, for example the displacement of the biological tissue. Also, in the case of calculating elasticity modulus in elasticity information calculating unit 23, the pressure information acquired by pressure measuring unit 29 connected to a pressure sensor (not shown in the diagram) of ultrasonic probe 2 is outputted to elasticity information calculating unit 23. Elasticity modulus is calculated by dividing variation of the pressure by variation of the strain.

For example, by setting the displacement measured by displacement calculating unit 22 as $L(X)$ and the pressure measured by pressure measuring unit 29 as $P(X)$, since strain $\Delta S(X)$ can be calculated by performing spatial differentiation on $L(X)$, elasticity modulus can be obtained using the equation: $\Delta S(X)=L(X)/\Delta X$. Also, Young's modulus $Ym(X)$ of elasticity modulus is calculated by the equation: $Ym=(\Delta P(X))/\Delta S(X)$. Since elasticity modulus of the biological tissue corresponding to each point of an image can be obtained by this Young's modulus $Ym$, a 2-dimensional elastic image can be continuously acquired. Young's modulus is the ratio of the simple tensile stress applied to an object to the strain generated parallel to the tensile.

Elastic image constructing unit 24 executes various image processing such as the smoothing process within the coordinate plane, contrast optimization process or the smoothing process in the time axis direction among the frames with respect to the calculated elasticity value (strain, elasticity modulus, etc.), and constructs 2-dimensional elastic image data.

Elasticity scan converter 25 has the function to execute coordinate system conversion on the 2-dimensional elastic image data outputted from elastic image constructing unit 24 for displaying by the display method of image display unit 13.

2-dimensional elastic image storing unit 26 stores the 2-dimensional elastic image data along with frame number "N".

In this manner, as shown in FIG. 4, RF signal frame data selecting unit 21 selects the RF signal frame data of the same frame numbers "1"~"n" in the raster address of the set range stored in storage media 200 and storage media 201 of RF signal frame data storing unit 20 respectively, and executes a series of processing in displacement calculating unit 22, elasticity information calculating unit 23, elastic image constructing unit 24 and elasticity scan converter 25 as mentioned above.

Figure 5:
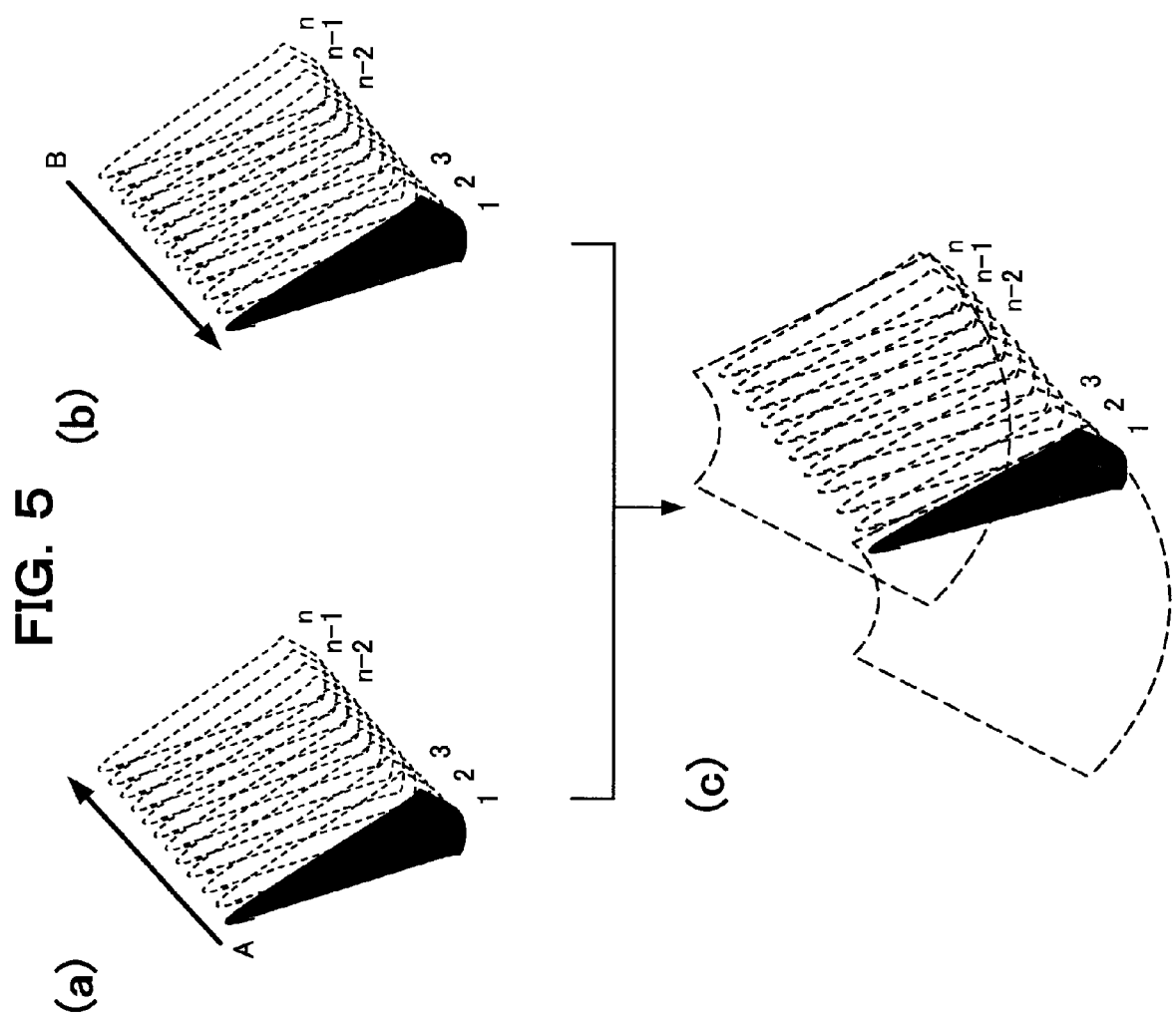
FIG. 5 shows the pattern for generating 2-dimensional elastic image data in the first embodiment of the present invention.
Figure 6:
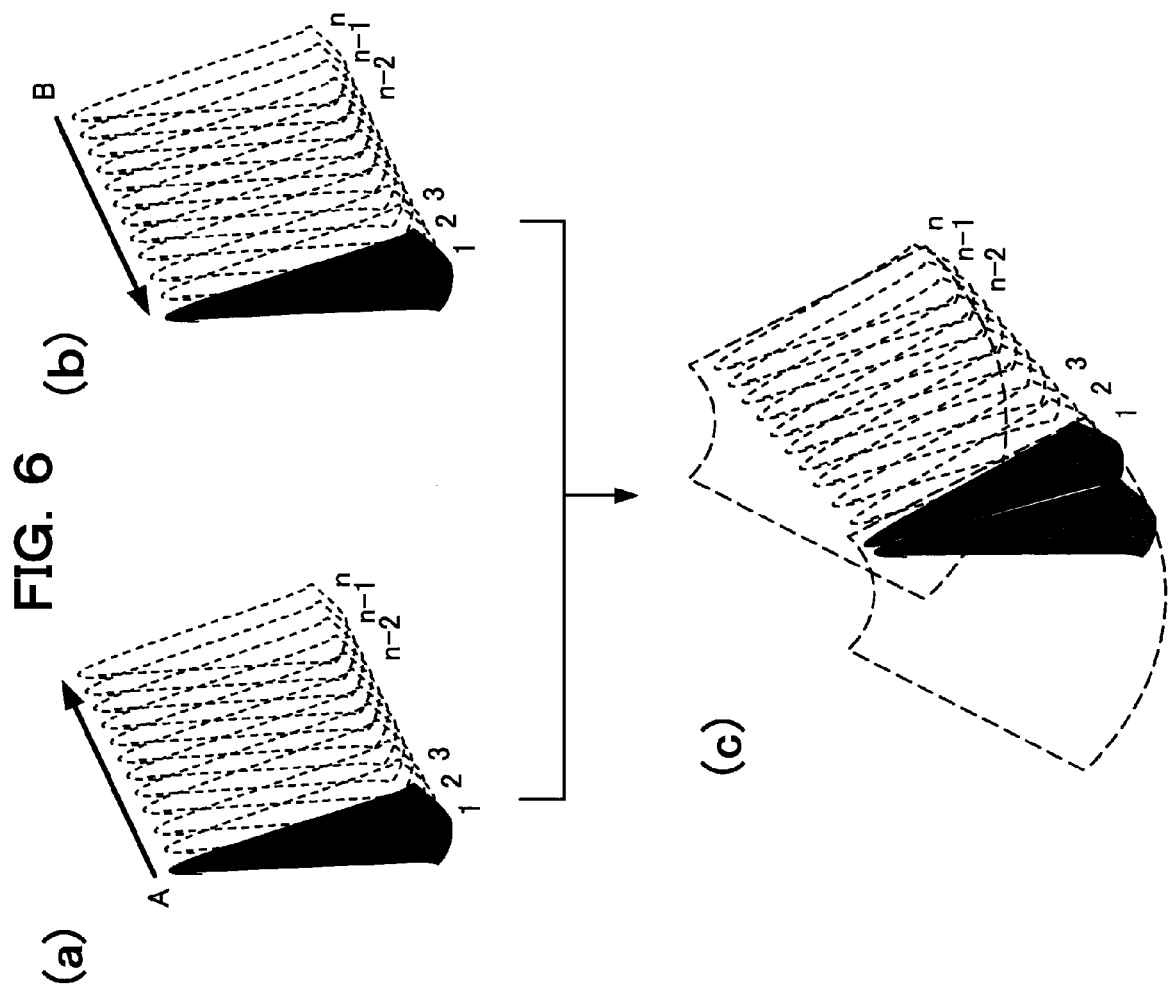
FIG. 6 shows the pattern for generating 2-dimensional elastic image in a second embodiment of the present invention.

2-dimensional elastic image storing unit 26 stores the 2-dimensional elastic image data of the raster address in the set range of a series of frame numbers "1"~"n". FIG. 5 shows the pattern for generating the 2-dimensional elastic image data of frame numbers "1"~"n". FIGS. 5(*a*) and (*b*) show the pattern that the RF signal frame data of frame numbers "1"~"n" in A-direction or B-direction is read out from storage media 200 and storage media 201, and FIG. 5(*c*) shows the condition that the 2-dimensional elastic image data of the raster address in the set range of frame numbers "1"~"n" is stored in 2-dimensional elastic image storing unit 26.

Elastic volume data generating unit 27 generates elasticity volume data from plural sets of 2-dimensional elastic image data in the raster address of the set range. The 2-dimensional elastic image data for the portion of n-frame stored in 2-dimensional elastic image storing unit 26 is read out, and the elastic volume data is generated by sequentially disposing the data for each scan plane. In this manner, the elastic volume data for rendering in the raster address of the set range which is the collection of 2-dimensional elastic image data in the object is constructed.

3-dimensional elastic image constructing unit 28 acquires image information on each point of the elastic volume data from the elasticity value (any one of strain, elasticity modulus, etc.) and the opacity corresponding to the respective points, and constructs a 3-dimensional elastic image. For example, a 3-dimensional elastic image is constructed using the volume rendering method by the equation below that calculates, in the depth direction, the elasticity value of the elastic volume data of the view point direction. The view point direction is the same direction as the view point direction in the volume rendering process, etc. in black and white 3-dimensional tomographic image constructing unit 11.

$$\alpha_{outi} = \alpha_{ini} + (1-\alpha_{ini}) \times \alpha_i$$

$$E_{outi} = E_{ini} + (1-\alpha_{ini}) \times \alpha_i \times E_i \quad \text{[Equation 2]}$$

$\alpha_{outi}$: output of the i-th opacity
$\alpha_{ini}$: input of the i-th opacity
$\alpha_i$: the i-th opacity
$E_{outi}$: output of the i-th elasticity value
$E_{ini}$: input of the i-th elasticity value
$E_i$: the i-th elasticity value Also, 3-dimensional elastic image constructing unit 28 appends light's three primary colors, i.e. red (R) value, green (G) value and blue (B) value to the image information that configures a 3-dimensional elastic image. The 3-dimensional elastic image constructing unit 28 appends, for example a red color code to the place having greater strain or smaller elasticity modulus compared to the surrounding area, and appends a blue color to the place having smaller strain or greater elasticity modulus compared to the surrounding area.

(Parallel Display/Superimposing Display)

Switching and synthesizing unit 12 is configured comprising an image memory, image processing unit and image selecting unit. Here, the image memory stores the black and white 3-dimensional tomographic image outputted from black and white 3-dimensional tomographic image constructing unit 11 and the color 3-dimensional elastic image in the raster address of the set range outputted from 3-dimensional elastic image constructing unit 28 along with time information.

Also, the image processing unit synthesizes the black and white 3-dimensional tomographic image data stored in the image memory and the color 3-dimensional elastic image data in the raster address of the set range by changing the synthesis ratio. Image processing unit reads out the black and white 3-dimensional tomographic image data and the color 3-dimensional elastic image data at the same viewpoint position from the image memory. While the image processing unit synthesizes the black and white 3-dimensional tomographic image data and the color 3-dimensional elastic image data, since the black and white 3-dimensional tomographic image data and the color 3-dimensional elastic image data are the image data after executing the volume rendering process, each set of data is actually added 2-dimensionally.

For example, as shown in the equations below, red (R) value, green (G) value and blue (B) value of the color 3-dimensional elastic image data and red (R) value, green (G) value and blue (B) value of the black and white 3-dimensional tomographic image data are added respectively in each point. In addition, $\alpha$ is the coefficient which is greater or equal to 0 and less or equal to 1, and can be set as desired via input unit 30.

$$\begin{aligned}
\text{(Synthetic image data } R) = & \quad \text{[Equation 3]} \\
& \alpha \times (\text{color 3-D elastic image data } R) + (1-\alpha) \times \\
& (\text{black and white 3-D tomographic image data } R) \\
\text{(Synthetic image data } G) = & \\
& \alpha \times (\text{color 3-D elastic image data } G) + (1-\alpha) \times \\
& (\text{black and white 3-D tomographic image data } G) \\
\text{(Synthetic image data } B) = & \\
& \alpha \times (\text{color 3-D elastic image data } B) + (1-\alpha) \times \\
& (\text{black and white 3-D tomographic image data } B)
\end{aligned}$$

For example, by setting the above-mentioned $\alpha$ as 0 or 1, it is possible to extract only the black and white 3-dimensional tomographic image data or the color 3-dimensional elastic image data. The image selecting unit selects the image to be displayed on image display unit 13 from among the black and white 3-dimensional tomographic image data in the volume memory, color 3-dimensional elastic image data in the raster address of the set range or the synthesized image data in the image processing unit.

Image display unit 13 displays the image synthesized by switching and synthesizing unit 12, black and white 3-dimensional tomographic image or color 3-dimensional elastic image in the raster address of the set range in parallel.

As described above, in accordance with the present embodiment, it is possible to construct and display a 3-dimensional elastic image showing hardness or softness of biological tissues in an object. Also, by calculating elasticity of each frame while narrowing down the setting range of raster address, it is possible to save time for elasticity calculation.

(Second Embodiment: Connecting)

Next, the second embodiment will be described referring to FIG. 1~FIG. 6. The difference from the first embodiment is that a 3-dimensional elastic image is constructed using the RF signal frame data in the adjacent raster address.

In the first embodiment, a 3-dimensional elastic image is constructed by storing the RF signal frame data in the raster address of the set range in storage media 200 and storage media 201. In the second embodiment, the RF signal frame data in the raster address of the range adjacent to the raster address of the range set in the first embodiment is further stored in storage media 200 and storage media 201, and a 3-dimensional elastic image is constructed while being connected to the 3-dimensional elastic image constructed in the first embodiment.

In concrete terms, the RF signal frame data in the raster address of "1"~"50" is stored in storage media 200 and storage media 201 in the first embodiment. Then in the second embodiment, the RF signal frame data in the raster address of "51"~"100" which is adjacent to the raster address of "1"~"50" is to be stored in storage media 200 and storage media 201.

Then as shown in FIG. 4, RF signal frame data selecting unit 21 selects the RF signal frame data in the raster address of the set range having the same frame numbers "1"~"n" stored in storage media 200 and storage media 201 of RF signal frame data storing unit 20 respectively, and executes a series of processing in displacement calculating unit 22, elasticity information calculating unit 23, elastic image constructing unit 24 and elasticity scan converter 25 in the same manner as in the first embodiment.

FIGS. 6(a) and (b) show the pattern that RF signal frame data in A-direction and B-direction having frame numbers "1"~"n" is read out from storage media 200 and storage media 201, and FIG. 6(c) shows the condition that the 2-dimensional elastic image data of frame numbers "1"~"n" is stored in 2-dimensional elastic image storing unit 26. In the present embodiment, 2-dimensional elastic image data in the raster address of "1"~"100" is stored in 2-dimensional elastic image storing unit 26.

Then elastic volume data generating unit 27 generates elastic volume data from plural sets of 2-dimensional elastic image data in the raster address of "1"~"100". The 2-dimensional elastic image data for the portion of n-frame stored in 2-dimensional elastic image storing unit 26 is read out, and elastic volume data is generated by sequentially disposing the data for each scan plane. In this manner, the elastic volume data in the raster address of "1"~"100" for the rendering which is the collection of the 2-dimensional elastic image data in an object is constructed.

3-dimensional elastic image constructing unit 28 acquires image information of each point in the elastic volume data from the elasticity value (any one of the strain, elasticity modulus, etc.) and the opacity corresponding to the respective points, and constructs a 3-dimensional elastic image.

Further, the RF signal frame data in the raster address of "101"~"150" can be stored in storage media 200 and storage media 201 for constructing a 3-dimensional elastic image.

As described above, in accordance with the present embodiment, a 3-dimensional elastic image can be constructed while being connected to the 3-dimensional elastic image of the raster address acquired previous time.

(Third Embodiment: Region of Interest (Manual))

Next, the third embodiment will be described referring to FIG. 1~FIG. 8. The difference from the first embodiment and the second embodiment is that the 3-dimensional elastic image is constructed from the elastic image that falls under the set region of interest.

Figure 7:
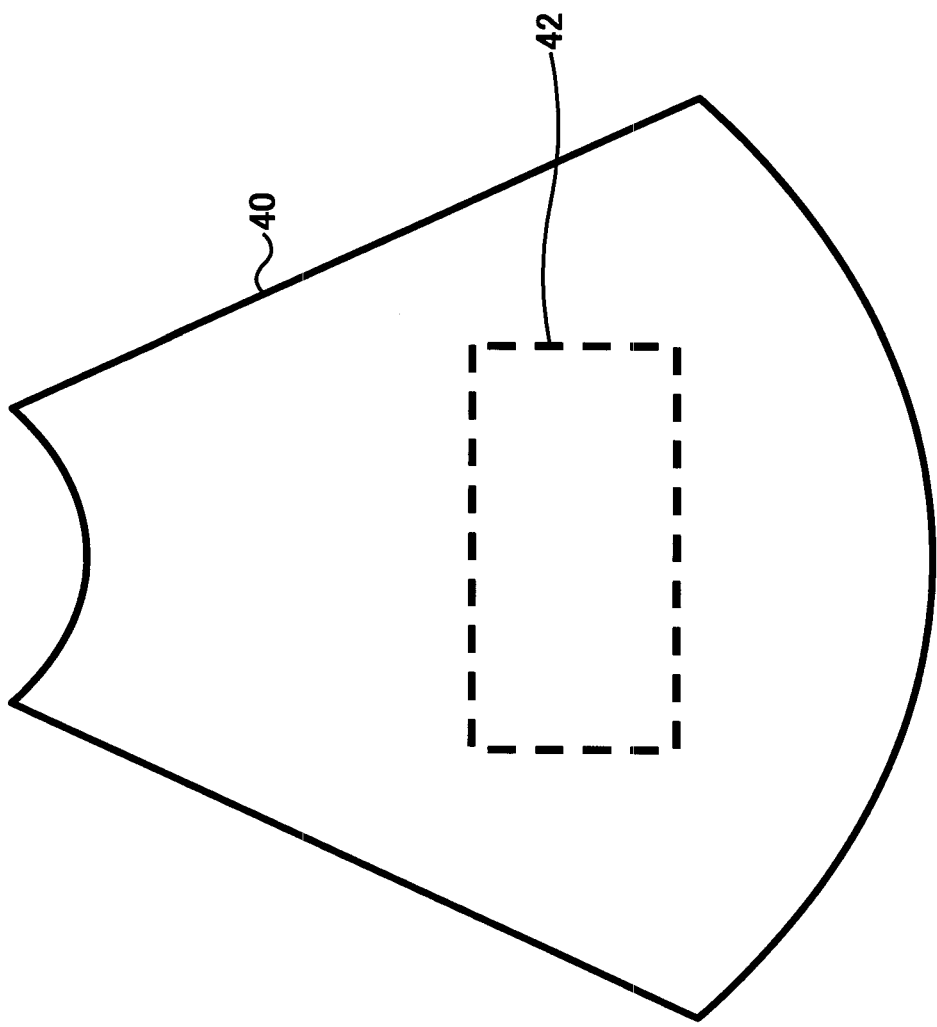
FIG. 7 shows a third embodiment of the present invention.
Figure 8:
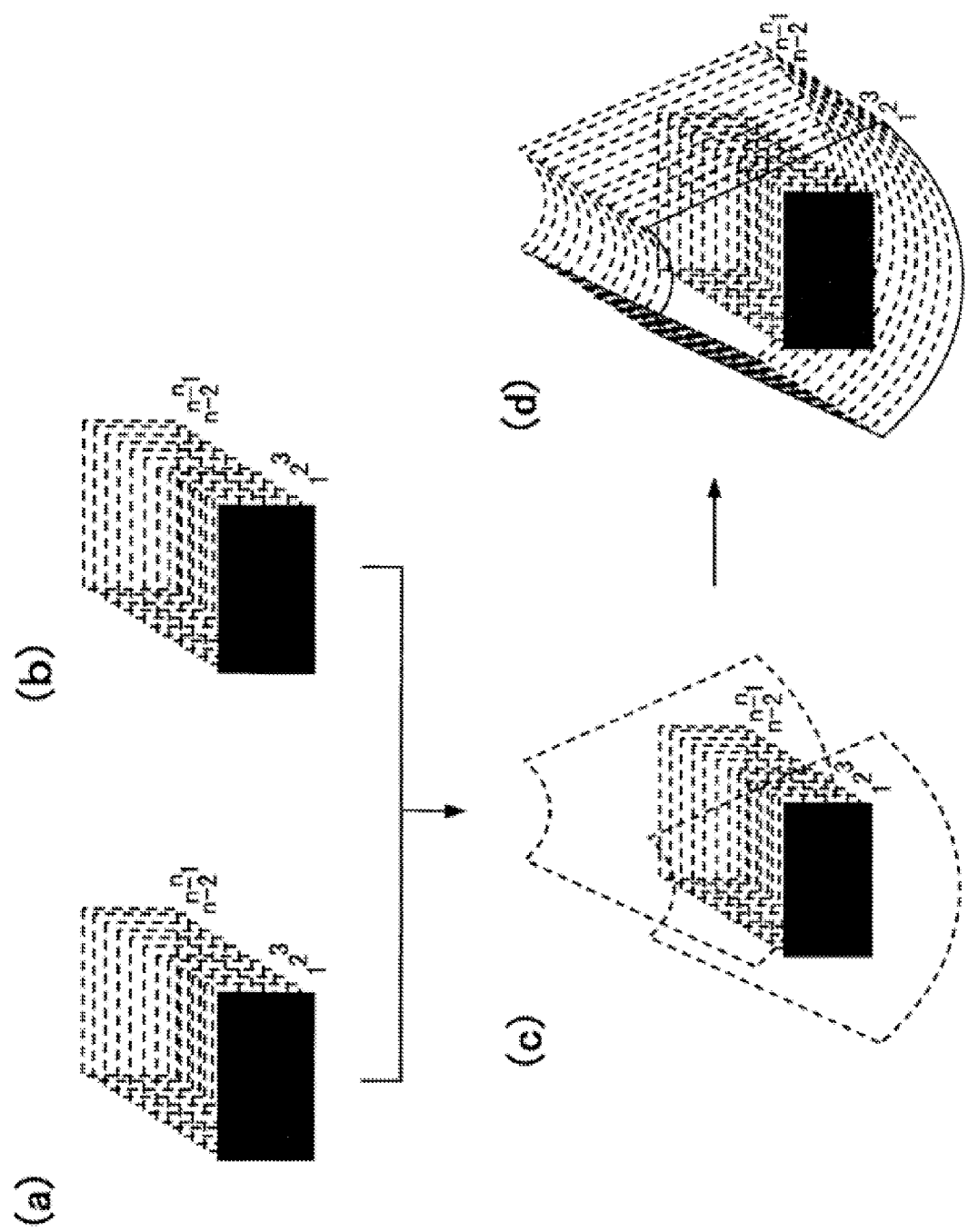
FIG. 8 shows the pattern for generating 2-dimensional elastic image data in a third embodiment of the present invention.

First, as shown in FIG. 2(b), region of interest 42 is set by input unit 30 on black and white 3-dimensional tomographic image 40 having any frame number out of "1"~"n" constructed by black and white 3-dimensional tomographic image constructing unit 11. In concrete terms, as shown in FIG. 7, region of interest 42 is determined using a button of input unit 30 after tracking a shape such as a circle, oval or rectangle using a trackball of input unit 30.

Then controller 31 informs the address (coordinate) of the border (dashed line part) of region of interest 42 to RF signal frame data storing unit 20. RF signal frame data storing unit 20 stores the RF signal frame data within the border of region of interest 42 in storage media 200 and storage media 201.

Then as shown in FIG. 4, RF signal frame data selecting unit 21 selects the RF signal frame data within the border of region of interest 42 having the same frame numbers "1"~"n" as the one stored in storage media 200 and storage media 201 of RF signal frame data storing unit 20 respectively, and executes a series of processing in displacement calculating unit 22, elasticity information calculating unit 23, elastic image constructing unit 24 and elasticity scan converter 25 as in the first embodiment.

FIGS. 8(a) and (b) show the pattern that the RF signal frame data of frame numbers "1"~"n" in A-direction and B-direction is read out from storage media 200 and storage media 201, and FIG. 8(c) shows the condition that the 2-dimensional elastic image data of frame numbers "1"~"n" is stored in 2-dimensional elastic image storing unit 26. In the present embodiment, the 2-dimensional elastic image data within the border of region of interest 42 is stored in 2-dimensional elastic image storing unit 26.

Then elastic volume data generating unit 27 generates elastic volume data from plural sets of 2-dimensional elastic image data within the border of region of interest 42. It reads out the 3-dimensional elastic image data for the portion of n-frame stored in 2-dimensional elastic image storing unit 26, and generates elastic volume data by sequentially disposing the data for each scan plane. In this manner, the elastic volume data within the border of region of interest 42 for the rendering which is the collection of 2-dimensional elastic image data in an object is constructed. 3-dimensional elastic image constructing unit 28 acquires image information in each point of the elastic volume data from the elasticity value (any one of strain, elasticity modulus, etc.) and the opacity corresponding to the respective points, and constructs a 3-dimensional elastic image. FIG. 8(c) shows the synthetic image in which the color 3-dimensional elastic image in region of interest 42 and the black and white 3-dimensional tomographic image are synthesized by switching and synthesizing unit 12.

As described above, in accordance with the present embodiment, it is possible to construct a 3-dimensional elastic image in region of interest 42. Also, by calculating elasticity of each frame by narrowing down the area to region of interest 42, elasticity calculation time can be shortened.

(Fourth Embodiment: ROI (Elasticity Information))

Next, the fourth embodiment will be described referring to FIGS. 1~11. The difference from the first~third embodiments is that the region of interest 50 or region of interest 70 is set using elasticity information and a 3-dimensional elastic image is constructed from the elasticity information of the set region of interest.

(Elasticity Modulus)

Figure 9:
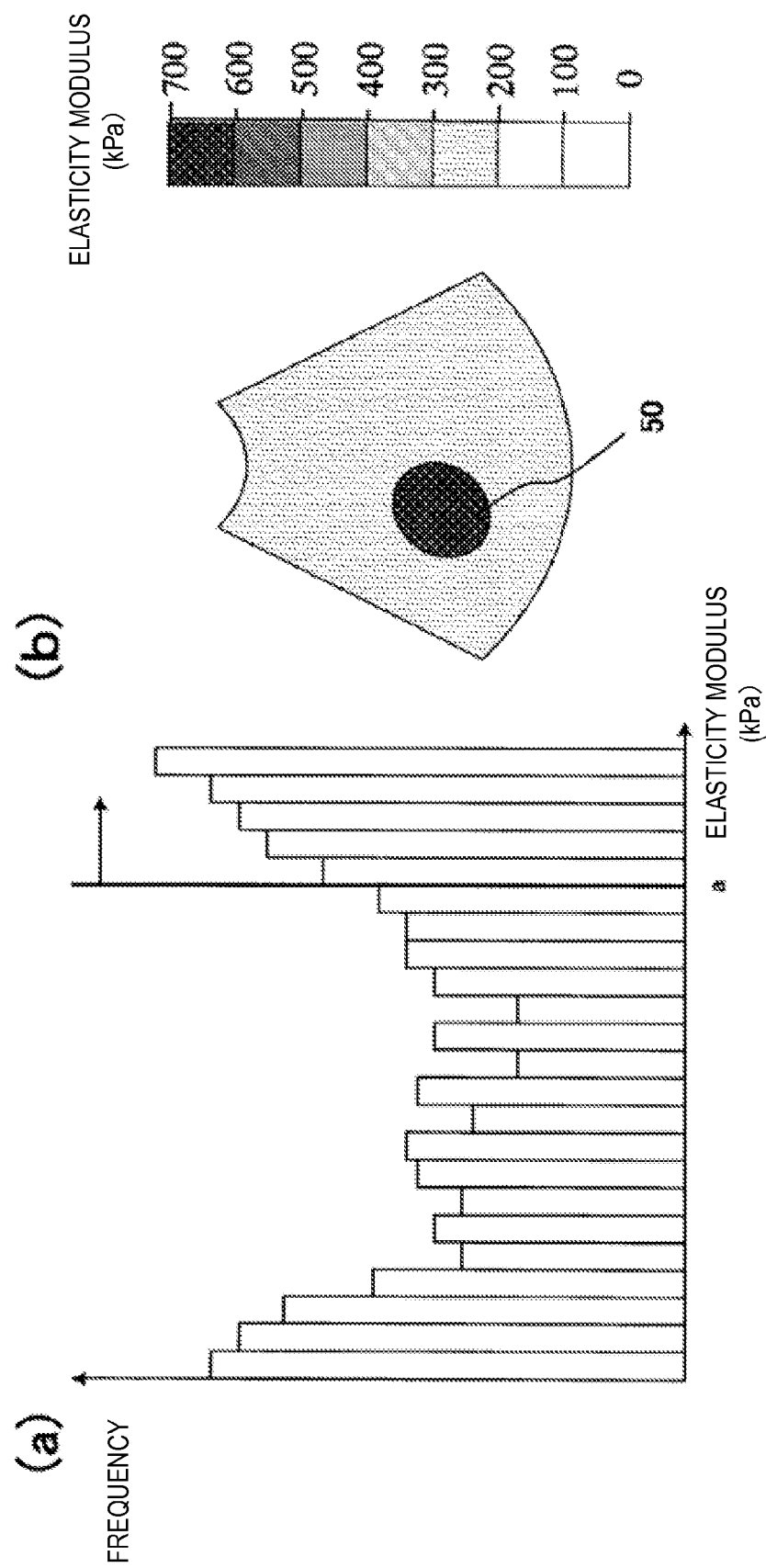
FIG. 9 shows a fourth embodiment of the present invention.
Figure 10:
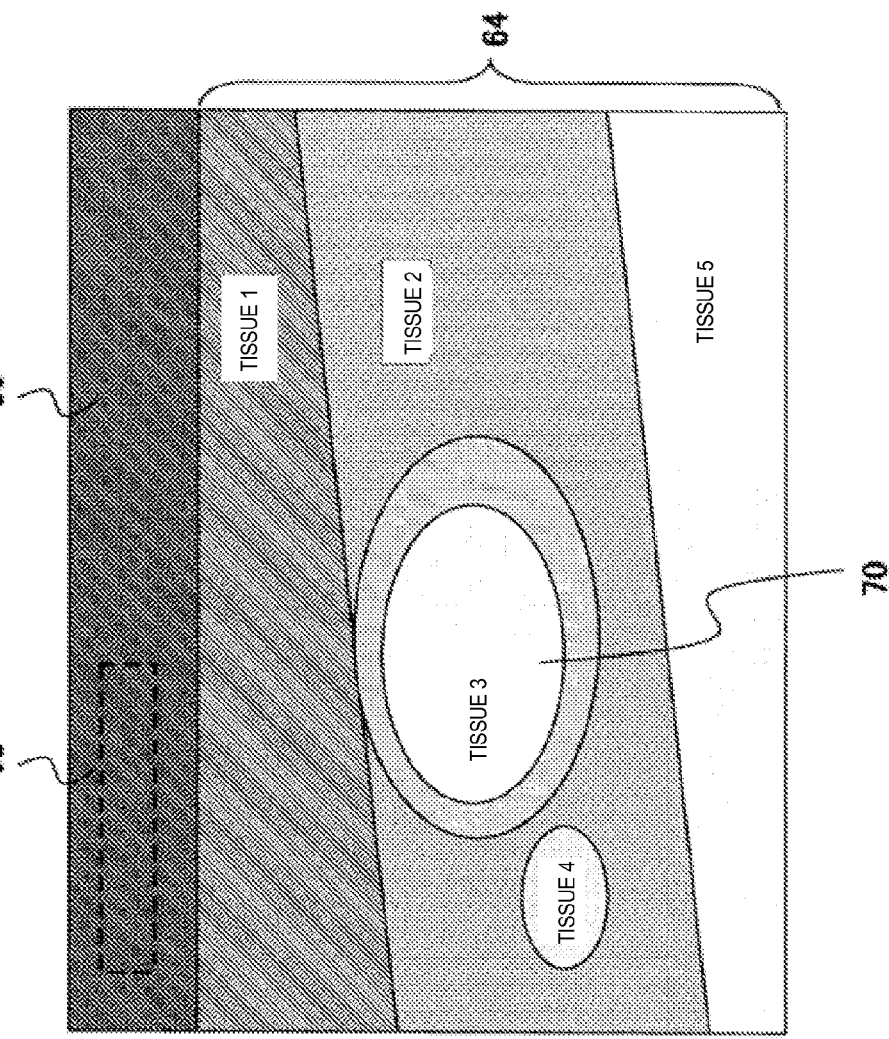
FIG. 10 shows the fourth embodiment of the present invention.

First, as shown in FIG. 9, the range of elasticity modulus desired to be extracted as region of interest 50 is set via input unit 30. Here, elasticity modulus is exemplified for explanation, but region of interest 50 may be set using strain or viscosity, etc.

As shown in FIG. 9(a), the range of elasticity modulus is set, for example as more or equal to "a" using input unit 30. The range of elasticity modulus may be set as more or equal to "a" and less or equal to "b". The "a" and "b" here are positive integers. Controller 31 causes elasticity information calculating unit 23 to specify the range where elasticity modulus is more or equal to "a" from the elasticity information corresponding to each point (coordinate) of frame numbers "1"~"n". As shown in FIG. 9(b), region of interest 50 having the elasticity modulus of more or equal to "a" is set to each frame having frame numbers "1"~"n".

(2 ROI Ratios)

Also, region of interest 70 may be set using the ratio of strain. As shown in FIG. 10(a), ultrasonic probe 2 is provided with pressing board 60 for pressing object 1 and reference deformable body 62 on the surface of pressing board 60. Reference deformable body 62 is formed by oil-based gel material, water-based gel material such as acrylamide, or silicon, etc.

Strain ratio in each point inside of object 1 is calculated based on the strain of reference deformable body 62. In concrete terms, as shown in FIG. 10(b), image region 66 of reference deformable body 62 is displayed in a tissue region nearest to ultrasonic probe 2 on an elastic image. Also, elastic image 64 in the respective tissues 1~5 is displayed on the lower part of reference deformable body 62. Reference region 68 is set on image region 66 of reference deformable body 62 via input unit 30. Then controller 31 causes elasticity information calculating unit 23 to calculate the strain ratio. Elasticity information calculating unit 23 obtains the ratio (index value $R_{i,j}$) between strain $\epsilon_{i,j}$ in each point i,j and reference strain $\epsilon_O$ by the equation below.

$$R_{i,j} = \epsilon_O/\epsilon_{i,j} \quad \text{[Equation 4]}$$

Then elasticity information calculating unit 23 extracts the region having index value $R_{i,j}$ which exceeds the reference value. The reference value can be arbitrarily set by input unit 30. Elasticity information calculating unit 23 sets the region having index value $R_{i,j}$ which exceeds the reference value as region of interest 70.

Also, elasticity information calculating unit 23 is capable of estimating the approximate elasticity modulus of the biological tissue in each point by measuring the elasticity modulus of reference deformable body 62 in advance. Elasticity information calculating unit 23 may set region of interest 70 based on the estimated elasticity modulus.

Then controller 31 informs the address (coordinate) of region of interest 50 or region of interest 70 set as described above to RF signal frame data storing unit 20. RF signal frame data storing unit 20 stores the RF signal frame data of region of interest 50 or region of interest 70 in storage media 200 and storage media 201.

Then as shown in FIG. 4, RF signal frame data selecting unit 21 selects the RF signal frame data in region of interest 50 or region of interest 70 having the same frame numbers "1"~"n" stored in storage media 200 and storage media 201 of RF signal frame data storing unit 20 respectively, and executes a series of processing in displacement calculating unit 22, elasticity information calculating unit 23, elastic image constructing unit 24 and elasticity scan converter 25 as in the first embodiment.

FIGS. 11(a) and (b) show the pattern that the RF signal frame data in A-direction and B-direction having the frame numbers "1"~"n" is readout from storage media 200 and storage media 201, and FIG. 11(c) shows the condition that the 2-dimensional elastic image data of frame numbers "1"~"n" is stored in 2-dimensional elastic image storing unit 26. In the present embodiment, the 2-dimensional elastic image data in region of interest 50 or region of interest 70 is stored in 2-dimensional elastic image storing unit 26.

Then elastic volume data generating unit 27 generates elastic volume data from plural sets of 2-dimensional elastic image data in region of interest 50 or region of interest 70. It reads out the 2-dimensional elastic image data for the portion of n-frame stored in 2-dimensional elastic image storing unit 26, and generates elastic volume data by sequentially disposing the data for each scan plane. In this manner, the elastic volume data in region of interest 50 or region of interest 70 for the rendering which is the collection of 2-dimensional elastic image data in the object is constructed. 3-dimensional elastic image constructing unit 28 acquires image information of each point in the elastic volume data from the elasticity value (any one of the strain, elasticity modulus, etc.) and the opacity corresponding to the respective points, and constructs a 3-dimensional elastic image.

As described above, in accordance with the present embodiment, it is possible to construct a 3-dimensional elastic image in region of interest 50 or region of interest 70 set by elasticity information.

Description of the Reference Numerals

1: object, 2: ultrasonic probe, 3: transmission unit, 4: reception unit, 5: ultrasonic transmission/reception controller, 6: phasing and adding unit, 7: tomographic image constructing unit, 8: black and white scan converter, 9: 2-dimensional tomographic image storing unit, 10: black and white volume data generating unit, 11: black and white 3-dimensional tomographic image constructing unit, 12: switching and adding unit, 13: image display unit, 20: RF signal frame data storing unit, 21: RF signal frame data selecting unit, 22: displacement calculating unit, 23: elasticity information calculating unit, 24: elastic image constructing unit, 25: color scan converter, 26: 2-dimensional elastic image storing unit, 27: elastic volume data generating unit, 28: color 3-dimensional elastic image constructing unit

The invention claimed is:

1. An ultrasonic diagnostic apparatus comprising:
an ultrasonic probe having transducers that transmit and receive ultrasonic waves;
a transmission unit configured to transmit ultrasonic waves to an object to be examined via the ultrasonic probe;
a reception unit configured to receive the reflected echo signals from the object;
an RF signal frame data storing unit configured to store one of a predetermined range of the RF signal frame data of a raster address and the RF signal frame data of the adjacent raster address adjacent to the raster address based on the reflected echo signals received by the reception unit;
an RF signal frame data selecting unit configured to select the predetermined range of RF signal frame data stored in the RF signal frame data storing unit;
an elasticity information calculating unit configured to calculate strain or elasticity modulus from the predetermined range of RF signal frame data of the raster address and the RF signal frame data of the adjacent raster address;
a 3-dimensional elastic image constructing unit configured to construct a 3-dimensional elastic image from plural sets of 2-dimensional elastic image data in the raster address and the adjacent raster address based on the calculated strain or elasticity modulus; and a display unit configured to display the 3-dimensional elastic image.

2. The ultrasonic diagnostic apparatus according to claim 1, wherein the predetermined range of RF signal frame data is set on the basis of the set range of a raster address of the ultrasonic wave.

3. The ultrasonic diagnostic apparatus according to claim 1, wherein the predetermined range of RF signal frame data is set on the basis of a region of interest set on the display unit.

4. The ultrasonic diagnostic apparatus according to claim 3, further comprising an input unit configured to input the region of interest.

5. The ultrasonic diagnostic apparatus according to claim 3, wherein the region of interest is set on the basis of the strain or elasticity modulus.

6. The ultrasonic diagnostic apparatus according to claim 3, wherein the region of interest is set on the basis of a ratio of the strain.

7. The ultrasonic diagnostic apparatus according to claim 1, wherein the ultrasonic probe is configured so that a transducer tilts in the direction orthogonal to the array direction of the plurality of transducers forming a rectangle or fan-shaped ultrasonic transmitting/receiving plane.

8. The ultrasonic diagnostic apparatus according to claim 7, wherein the ultrasonic probe has a position sensor that measures the tilt of the transducer, and outputs the tilt of the transducer as a frame number.

9. The ultrasonic diagnostic apparatus according to claim 1, wherein the RF signal frame data storing unit comprises storage media configured to store a series of RF signal frame data to be scanned in one direction along with the frame number corresponding to the tilt of the transducer.

10. The ultrasonic diagnostic apparatus according to claim 9, wherein the RF signal frame data selecting unit selects the RF signal frame data having the same frame number stored in the RF signal frame data storing unit respectively.

11. The ultrasonic diagnostic apparatus according to claim 1, further comprising:
a tomographic image constructing unit configured to construct tomographic image data from the RF signal frame data;
a tomographic volume data generating unit configured to generate tomographic volume data from plural sets of the tomographic image data; and
a 3-dimensional elastic image constructing unit configured to construct a 3-dimensional elastic image from the tomographic image data.

12. An ultrasonic image display method including:
a step of transmitting/receiving ultrasonic waves to/from an object to be examined;
a step of storing a predetermined range of RF signal frame data of a raster address and the RF signal frame data of the adjacent raster address adjacent to the raster address based on the reflected echo signal received by the reception unit;
a step of selecting at least two sets of RF signal frame data in a predetermined range stored in the RF signal frame data storing unit;
a step of calculating strain or elasticity modulus from a part of the selected predetermined range of RF signal frame data of the raster address and RF signal frame data of the adjacent raster address; and
a step of constructing and displaying a 3-dimensional elastic image from plural sets of 2-dimensional elastic image data in the raster address and the adjacent raster address based on the calculated strain or elasticity modulus.

13. The ultrasonic diagnostic apparatus according to claim 1, wherein the 3-dimensional elastic image in the adjacent raster address is constructed while being connected to the 3-dimensional elastic image in the raster address acquired previous time.

* * * * *